(12) United States Patent
Hillbratt

(10) Patent No.: US 9,554,218 B2
(45) Date of Patent: Jan. 24, 2017

(54) AUTOMATIC SOUND OPTIMIZER

(75) Inventor: Martin Hillbratt, Lindome (SE)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 13/562,601

(22) Filed: Jul. 31, 2012

(65) Prior Publication Data

US 2014/0039576 A1  Feb. 6, 2014

(51) Int. Cl.
*A61N 1/05* (2006.01)
*H04R 25/00* (2006.01)
*A61N 1/36* (2006.01)

(52) U.S. Cl.
CPC .......... *H04R 25/505* (2013.01); *A61N 1/0541* (2013.01); *A61N 1/36032* (2013.01); *H04R 25/43* (2013.01); *H04R 2225/43* (2013.01)

(58) Field of Classification Search
CPC  A61N 1/36032; A61N 1/0541; H04R 25/505; H04R 25/70; H04R 25/43; H04R 225/025
USPC .................................................. 607/55–57
See application file for complete search history.

(56) References Cited

U.S. PATENT DOCUMENTS

| 6,658,122 | B1 * | 12/2003 | Westermann | H04R 25/70 381/312 |
| 2007/0135862 | A1 * | 6/2007 | Nicolai | A61N 1/36032 607/56 |
| 2009/0046878 | A1 | 2/2009 | Sorgel et al. | |
| 2009/0157143 | A1 * | 6/2009 | Edler et al. | 607/57 |
| 2009/0304215 | A1 | 12/2009 | Hansen | |
| 2010/0234920 | A1 * | 9/2010 | Saoji et al. | 607/57 |
| 2011/0125218 | A1 * | 5/2011 | Busby | 607/57 |

FOREIGN PATENT DOCUMENTS

| JP | 2007235364 A | 9/2007 |
| KR | 1020060062343 A | 6/2006 |

OTHER PUBLICATIONS

International Search Report and Written Opinion for PCT/IB2013/056234 dated Feb. 27, 2014.

* cited by examiner

*Primary Examiner* — Michael Kahelin
*Assistant Examiner* — Minh Duc Pham
(74) *Attorney, Agent, or Firm* — McDonnell Boehnen Hulbert & Berghoff LLP

(57) ABSTRACT

Disclosed herein are systems and methods that help to optimize the sound quality produced when a sound processing mode is enabled in an audio device, such as a hearing prosthesis. When the sound processing mode is enabled, a sound processor in the audio device will create a candidate transformed signal based on a default set of parameters associated with the sound processing mode (i.e. a candidate signal processing function). Further, the sound processor will create a reference transformed signal based on the same enabled sound processing mode, but with a varied set of parameters (i.e. a modified signal processing function). The sound processor will then compare the candidate transformed signal to the reference transformed signal to determine which signal has a higher quality. The device then creates an output based on the higher quality signal.

27 Claims, 4 Drawing Sheets

AUTOMATIC SOUND OPTIMIZER

BACKGROUND

Various types of hearing prostheses may provide people having different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea, where sound vibrations are converted into neural signals, or any other part of the ear, auditory nerve, or brain that may process the neural signals.

People with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sound into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids may include bone anchored hearing aids, direct acoustic cochlear stimulation devices, or other vibration-based devices.

A bone anchored hearing aid typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing aids may use similar vibration mechanisms to transmit sound via direct vibration of teeth or other cranial or facial bones.

Each type of hearing prosthesis has an associated sound processor. In one basic type of hearing prosthesis, the sound processor may just provide an amplification to any sounds received by the prosthesis. However, in other applications, the processor present in a hearing prosthesis may be more advanced. For example, some processors may be programmable and include advanced signal processing functions (e.g., noise reduction functions).

SUMMARY

A traditional hearing prosthesis will receive an input signal, process the input signal, and create an output. Generally, upon receipt of the input signal, the hearing prosthesis uses a microphone to convert an acoustic wave into an electrical signal. Applying parameters associated with a sound processing mode, a sound processor of the prosthesis then transforms the electrical signal into a transformed signal, and the prosthesis produces an output based on the transformed signal.

Advantageously, in the disclosed systems and methods the processor works on an ongoing basis to optimize this transformation, by separately transforming the input signal using two different transformation functions and selecting the highest quality output from those functions.

The disclosed systems and methods, when operating in a particular sound-processing mode, cause the processor to transform the input signal into a candidate transformed signal by applying a candidate signal processing function having parameter values specific to the sound-processing mode.

At the same time, however, the processor also transforms the input signal into a reference transformed signal by applying a modified signal processing function, which may be the same as the candidate signal processing function but have different parameter values or may be different than the candidate signal processing function. The processor then compares the reference transformed signal with the candidate transformed signal to determine which is higher quality. If the processor determines that the candidate transformed signal is higher quality, then the processor outputs the candidate transformed signal as the transformed signal. On the other hand, if the processor determines that the reference transformed signal is higher quality, then the processor outputs the reference transformed signal as the transformed signal. The prosthesis then provides an output based on that transformed signal.

DETAILED DESCRIPTION

1. Overview

Figure 1A:
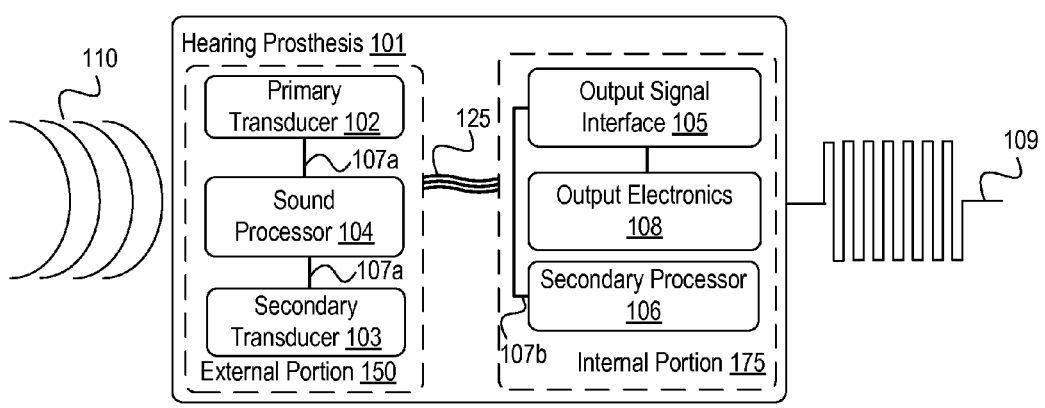
FIG. 1A is a simplified block diagram of an example a hearing prosthesis.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Disclosed herein are systems and methods that help to optimize the sound quality produced when a sound processing mode is enabled in a hearing prosthesis. When the sound processing mode is enabled, a sound processor of the hearing prosthesis will create a candidate transformed signal based on a default set of parameters associated with the sound processing mode (i.e. a candidate signal processing function). Further, the sound processor will create a reference transformed signal based on the same enabled sound processing mode, but with a varied set of parameters (i.e. a modified signal processing function). The sound processor will then compare the candidate transformed signal to the reference transformed signal to determine which signal has a higher quality. And the prosthesis will then create an output based on the higher quality signal.

During operation of the hearing prosthesis, the sound processor initially creates an output based on the candidate transformed signal. However, if the sound processor determines that the quality of the reference transformed signal is better than the quality of the candidate transformed signal, the processor will substitute the modified signal processing function for the candidate signal processing function in order to create a higher quality output. In other words, the parameters of the modified signal processing function will be substituted for the parameters of the candidate signal processing function. Because the signal of the hearing prosthesis is based on the candidate signal processing function, changing the candidate signal processing function parameters to be the modified signal processing function parameters causes a responsive change in the output. Hence, the output changes to match the reference transformed signal that was determined to have a higher quality.

Alternatively, if the sound processor determines that the quality of the reference transformed signal is not better than the quality of the candidate transformed signal, the processor will continue to provide the candidate transformed signal as the output. Thus, the output of the hearing prosthesis will continue to be based on the candidate transformed signal.

A sound processor in the hearing prosthesis has a variety of sound processing modes. Each respective sound processing mode functions to transform an input signal into an output based on processing parameters specific to the respective sound processing mode. For example, if a hearing prosthesis is in a windy environment, the sound processor may operate in a wind-noise reduction mode. In this example mode, the sound processor identifies parameters of the received signal that indicate at least a portion of the received signal as wind noise. The sound processor will then responsively remove aspects of the signal associated with wind noise to create an output.

In some embodiments, the sound processor can operate in a variety of sound processing modes. A subset of example sound processing modes includes wind-noise reduction mode, beam-forming mode, voice enhancement mode, feedback reduction mode, compression timing mode, and music mode. Each sound processing mode initially defines one or more signal processing parameters. However, during the operation of the hearing prosthesis, the processor can vary the parameters associated with each sound processing mode.

In one embodiment, each of the various sound processing modes will have a static set of parameters with which to transform the input signal. For example, the wind-noise reduction mode is either switched on or switched off as selected by a recipient of the prosthesis. When the wind-noise reduction mode is switched on, the processor will then have a static (or fixed) set of parameters that it can apply to the received signal. Accordingly, when enabled, each mode of the hearing prosthesis will cause the processor to apply a static set of parameters to an input signal to transform the input signal to an output.

In another aspect, the processor will iteratively vary the parameters specific to the modified signal processing function for a given sound processing mode. For example, the processor will iteratively adjust the gain on a specific frequency band in order to improve the sound quality of a sound the prosthesis recipient is trying to hear. After each iteration, the processor will responsively determine if a revised parameter from the iterative adjustment creates an improved (e.g., higher quality) output.

Further, the sound processor will continue to iteratively vary parameters specific to the modified signal processing function. In one embodiment, during the operation of the hearing prosthesis, the prosthesis performs iterations of the parameters continuously. In another embodiment, the hearing prosthesis performs iterations of the parameters at specific time intervals. In a further embodiment, the hearing prosthesis performs iterations of the parameters when the ambient audio conditions change. For example, the hearing prosthesis will detect a change in the ambient audio conditions, such as the change in ambient audio conditions when a prosthesis recipient walks into a noisy room, and responsively iterate the parameters to help to optimize sound quality.

In addition to having a sound processor, the hearing prosthesis also has a first microphone arranged to receive an audio signal, and output circuitry for providing an output to a recipient of the hearing prosthesis. Particularly, the processor in the hearing prosthesis receives a input signal, having one or more audio attributes, representing the audio received by the first microphone. Further, the processor responsively transforms the input signal into an output. The transformation adjusts the input signal based on a given sound processing mode and its associated parameters. Finally, the output circuitry provides the output based on the output.

Additionally, in some embodiments, the hearing prosthesis includes a second microphone. Similar to the first microphone, the second microphone receives audio and creates an input signal. During operation of the prosthesis, the sound processor transforms the second audio signal into an output based on the sound processing mode.

In some additional embodiments, the hearing prosthesis will create a single candidate transformed signal based on a combination of both the signal from the first microphone as well as the signal from the second microphone. Thus, in these additional embodiment, to create the single candidate transformed signal, the sound processor will combine the two input signals. For example, a beam forming algorithm may receive both audio signal inputs and create a single output from the two inputs.

In further embodiments, a sound processor located within the hearing prosthesis will perform the sound processing. However, in some other embodiments, the sound processor is located in a computer external to a hearing prosthesis device. For example, the computer may be a standard computer, a laptop computer, a tablet computing device, a mobile device such as a cellular phone, or a custom computing device. Thus, the prosthesis may include a computing device external to the body-worn prosthesis unit.

2. Sample Systems

For illustration purposes, some systems and methods of are described with respect to cochlear implants. However, many systems and methods are equally applicable to other types of hearing prostheses. Certain aspects of the disclosed systems and methods could be applicable to any type of hearing prosthesis now known or later developed. Further, some of the disclosed methods can be applied to other acoustic devices that are not necessarily hearing prostheses. For example, the methods may be adapted for use in portable audio player.

FIG. 1A shows one example of a hearing prosthesis 101 configured according to some embodiments of the disclosed systems and methods. The hearing prosthesis 101 may be a cochlear implant, an acoustic hearing aid, a bone anchored hearing aid or other vibration-based hearing prosthesis, a direct acoustic stimulation device, an auditory brain stem implant, or any other type of hearing prosthesis configured to receive and process at least one signal from an audio transducer of the prosthesis.

The example hearing prosthesis 101 includes an external portion 150 and an internal portion 175. The external portion 150 includes a primary transducer 102, a secondary transducer 103, and a sound processor 104, all of which are connected directly or indirectly via circuitry 107a. The internal portion 175 includes an output signal interface 105, output electronics 108, and a secondary processor 106, all of which connect directly or indirectly via circuitry 107b. In other embodiments, the hearing prosthesis 101 may have additional or fewer components than the prosthesis shown in FIG. 1. For example, secondary transducer 103 will be omitted in some embodiments. Additionally, the components may be arranged differently than shown in FIG. 1. For example, depending on the type and design of the hearing prosthesis, the illustrated components may be enclosed within a single operational unit or distributed across multiple operational units (e.g., an external unit and an internal unit). Similarly, in some embodiments, the hearing prosthesis 101 will additionally include one or more processors (not shown) configured to determine various settings for either sound processor 104 or secondary processor 106.

In embodiments where the hearing prosthesis 101 is a cochlear implant, the hearing prosthesis comprises an external portion 150 worn outside the body and an internal portion 175 worn inside the body. The external portion 150 is coupled to the internal portion 175 via an inductive coupling pathway 125. The external portion 150 houses a primary transducer 102 and a sound processor 104. The primary transducer 102 receives acoustic signals 110, and the sound processor 104 analyzes and encodes the acoustic signals 110 into a group of electrical stimulation signals 109 for application to an implant recipient's cochlea via an output signal interface 105 communicatively connected to output electronics 108.

In some embodiments, the sound processor 104 will be located in another separate external portion (not shown). For example, the sound processor 104 may be located in a standard computer, a laptop computer, a tablet computing device, a mobile device such as a cellular phone, or a custom computing device. The primary transducer 102 will wirelessly communicate signals to the sound processor 104. Further, the external portion 150 may also include a secondary transducer 103. The secondary transducer 103 may be the same type of transducer as the primary transducer 102. However, in some embodiments, the secondary transducer 103 is a different type of transducer than the primary transducer 102. For example, if both transducers are microphones, each may have a different beam pattern.

For a cochlear implant, the output electronics 108 are an array of electrodes. Individual sets of electrodes in the array of electrodes are grouped into stimulation channels. Each stimulation channel has at least one working electrode (current source) and at least one reference electrode (current sink). During the operation of the prosthesis, the cochlear implant applies electrical stimulation signals to a recipient's cochlea via the stimulation channels. It is these stimulation signals that cause the recipient to experience sound sensations corresponding to the sound waves received by the primary transducer 102 and encoded by the processor 104.

Figure 1B:
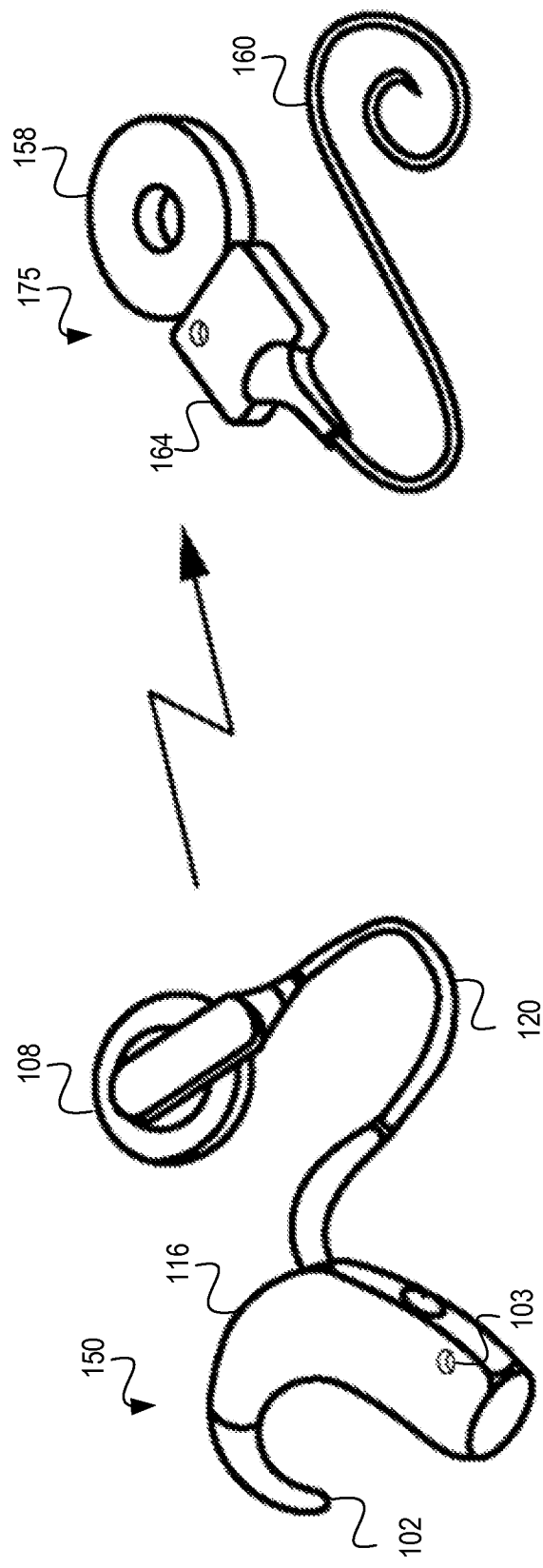
FIG. 1B shows an example of an external portion of a cochlear implant coupled to an internal portion of the cochlear implant.

FIG. 1B shows an example of an external portion 150 of a cochlear implant communicatively coupled to the internal portion 175 of the cochlear implant. The external portion 150 of a cochlear implant is directly attached to the body of a recipient and the internal portion 175 is implanted in the recipient. The external portion 150 typically comprises a housing 116 which has incorporated a primary transducer 102 for detecting sound, a sound processing unit (104 of FIG. 1A), an external coil 108 including a radio frequency modulator (not shown) and a coil driver (not shown), and a power source (not shown). External coil 108 is connected with a transmitter unit and the housing 116 by a wire 120. The housing 116 may be shaped so that it can be worn and held behind the ear. In some embodiments, the external portion 150 also features a secondary transducer 103. The speech processing unit in the housing 116 processes the output of the transducer 102 and generates coded signals which are provided to the external coil 108 via the modulator and the coil driver.

The internal portion 175 comprises a housing 164. Located within housing 164 are a receiver unit (not shown), a stimulator unit (not shown), an external portion sensor (not shown), a power source (not shown), and a secondary processor (106 of FIGS. 1A). Attached to the housing 164 are an internal coil 158 and an electrode assembly 160 that can be inserted in the cochlea. Magnets (not shown) typically secure the internal (receiving) coil 158 and the external (transmitting) coil 108 so that the external coil 108 can be positioned and secured via the magnets outside the recipient's head aligned with the implanted internal coil 158 inside the recipient's head. The internal coil 158 receives power and data from the external coil 108.

The internal portion 175 has a power source, such as a battery or capacitor, to provide energy to the electronic components housed within the internal portion 175. In some embodiments, the external portion 150 inductively charges the power source within the internal portion 175. In an example embodiment, a power source that is part of the external portion 150 is the primary power source for the hearing prosthesis. In this example, the power source within the internal portion 175 functions only as a backup source of power. The battery in the internal portion 175 is used as a backup power source when either the external portion 150 runs out of power or when the external portion 150 is decoupled from the internal portion 175. The electrode assembly 160 includes a cable that extends from the implanted housing 164 to the cochlea and terminates in the array of electrodes. Transmitted signals received from the internal coil 158 are processed by the receiver unit in the housing 164 and are provided to the stimulator unit in the housing 164.

The external coil 108 is held in place and aligned with the implanted internal coil via the noted magnets. In one embodiment, the external coil 108 transmits electrical signals to the internal coil via a radio frequency (RF) link. In some embodiments, the external coil 108 transmits electrical signals to the internal coil via a magnetic (or inductive) coupling.

Figure 2:
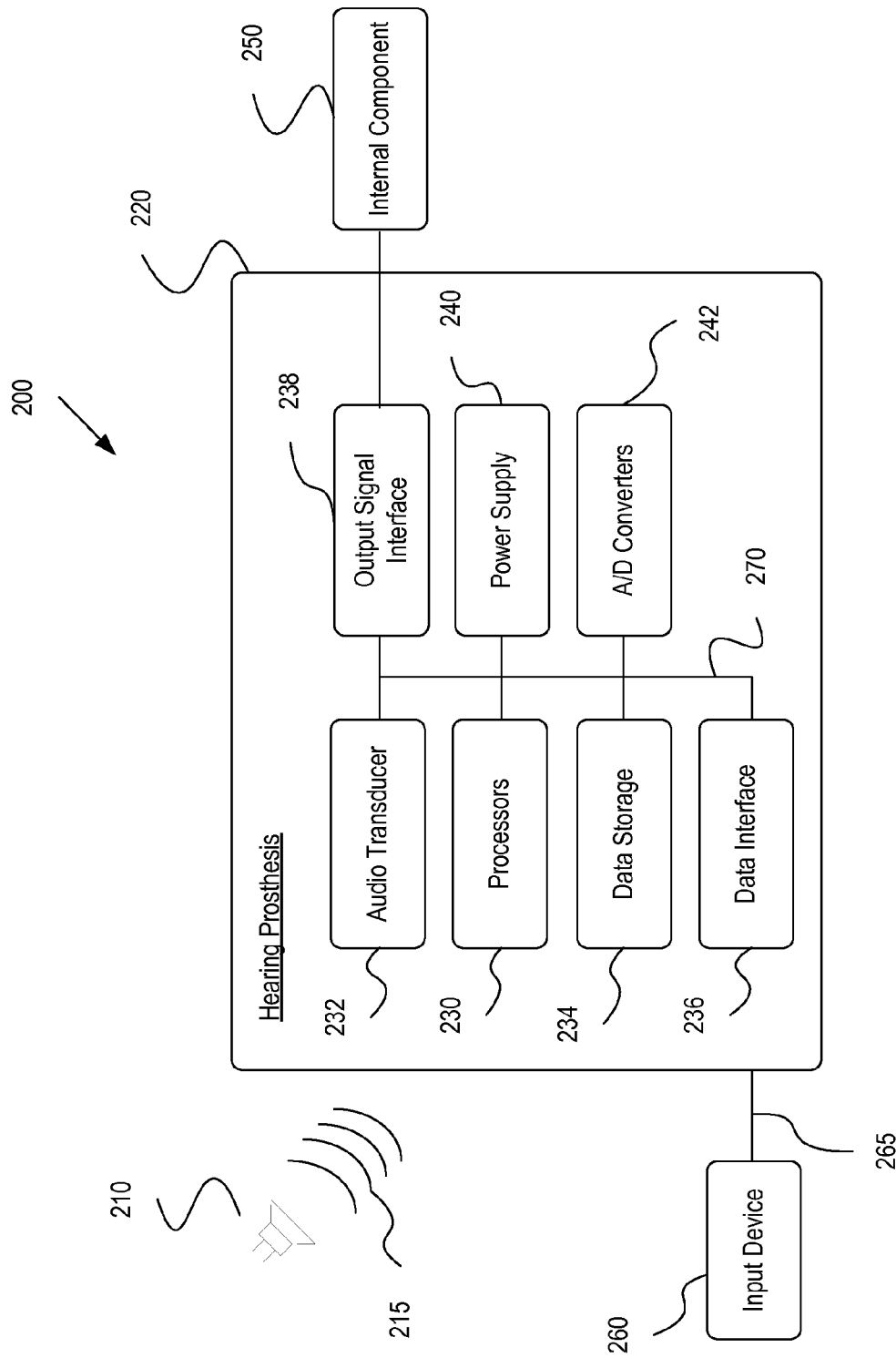
FIG. 2 is a simplified block diagram of an example a hearing prosthesis configured according to some embodiments of the disclosed methods.

FIG. 2 shows one example system 200 that includes a hearing prosthesis 220 configured according to some embodiments of the disclosed methods, systems, and hearing prostheses. In an exemplary embodiment, the hearing prosthesis 220 is a cochlear implant. In other embodiments, the hearing prosthesis 220 is a bone-anchored device, a direct acoustic stimulation device, an auditory-brain-stem implant, an acoustic hearing aid, or any other type of hearing prosthesis configured to assist a prosthesis recipient in perceiving sound.

The hearing prosthesis 220 illustrated in FIG. 2 includes a data interface 236, at least one audio transducer 232, one or more processors 230, an output signal interface 238, data storage 234, at least one analog-to-digital converter 242, and a power supply 240, all of which are illustrated as being connected directly or indirectly via a system bus or other circuitry 270. Further, in some embodiments, the one or more processors 230 are located within a hearing prosthesis device or located in an external computing device.

The power supply 240 supplies power to various components of the hearing prosthesis 220 and can be any suitable power supply, such as a non-rechargeable or rechargeable battery. In one example, the power supply 240 is a battery that can be recharged wirelessly, such as through inductive charging. Such a wirelessly rechargeable battery would facilitate complete subcutaneous implantation of the hearing prosthesis 220 to provide a fully implantable prosthesis. A fully implanted hearing prosthesis has the added benefit of enabling the recipient to engage in activities that expose the recipient to water or high atmospheric moisture, such as swimming, showering, etc., without the need to remove, disable or protect, such as with a water/moisture proof covering or shield, the hearing prosthesis.

The data storage 234 generally includes any suitable volatile and/or non-volatile storage components. Further, in some embodiments, the data storage 234 includes computer-readable program instructions and perhaps additional data. In some embodiments, the data storage 234 stores an amplitude response, a phase response, and recipient-specific parameters associated with the hearing prosthesis 220. Additionally, the data storage 234 stores a set of signal processing modes and associated parameters for each respective signal processing mode. In other embodiments, the data storage 234 also includes instructions used to perform at least part of the disclosed methods and algorithms, such as method 300.

In other embodiments, at least one analog-to-digital converter receives the input signal from that at least one audio transducer 232 via the system bus or other known circuitry 270. In such embodiments, the one or more processors comprise a digital signal processor or similar processor suitable for processing digital audio signals.

In the illustrated example, the at least one audio transducer 232 are omnidirectional microphones. In alternative embodiments, the at least one audio transducer 232 comprise directional microphone(s), omnidirectional microphone(s), electro-mechanical transducer(s), and/or any other audio transducer(s) or combination of audio transducers suitable for receiving audio signals for the hearing prosthesis utilized. The at least one audio transducer 232 receives, for example, an audio signal 215 from a target source 210 and supply input signal to the one or more processors.

In the present example, the one or more processors 230 are configured to operate in at least one sound processing mode. One example sound processing mode is a wind-noise reduction mode. In some circumstances, the audio transducer also receives wind noise and/or other noise, which is included in the input signal. This is accomplished, for example, by subtracting a signal representing wind noise from the input signal. However, in other examples other methods may be used to remove the wind noise from the input signal.

If the one or more processors 230 do not detect the presence of wind noise, then the input signals are processed using a normal (or default) mode of operation. However, if the one or more processors 230 detect the presence of wind noise, the one or more processors 230 implement a wind-noise reduction signal processing. The one or more processors 230 will operate in a wind-noise reduction mode and determine a quality associated with the output created when operating in wind-noise reduction mode. The one or more processors 230 transmit the output to the output signal interface 238. The output signal interface 238 then transmits the signal to an internal component 250 for delivery to the recipient of the hearing prosthesis 220.

Figure 3:
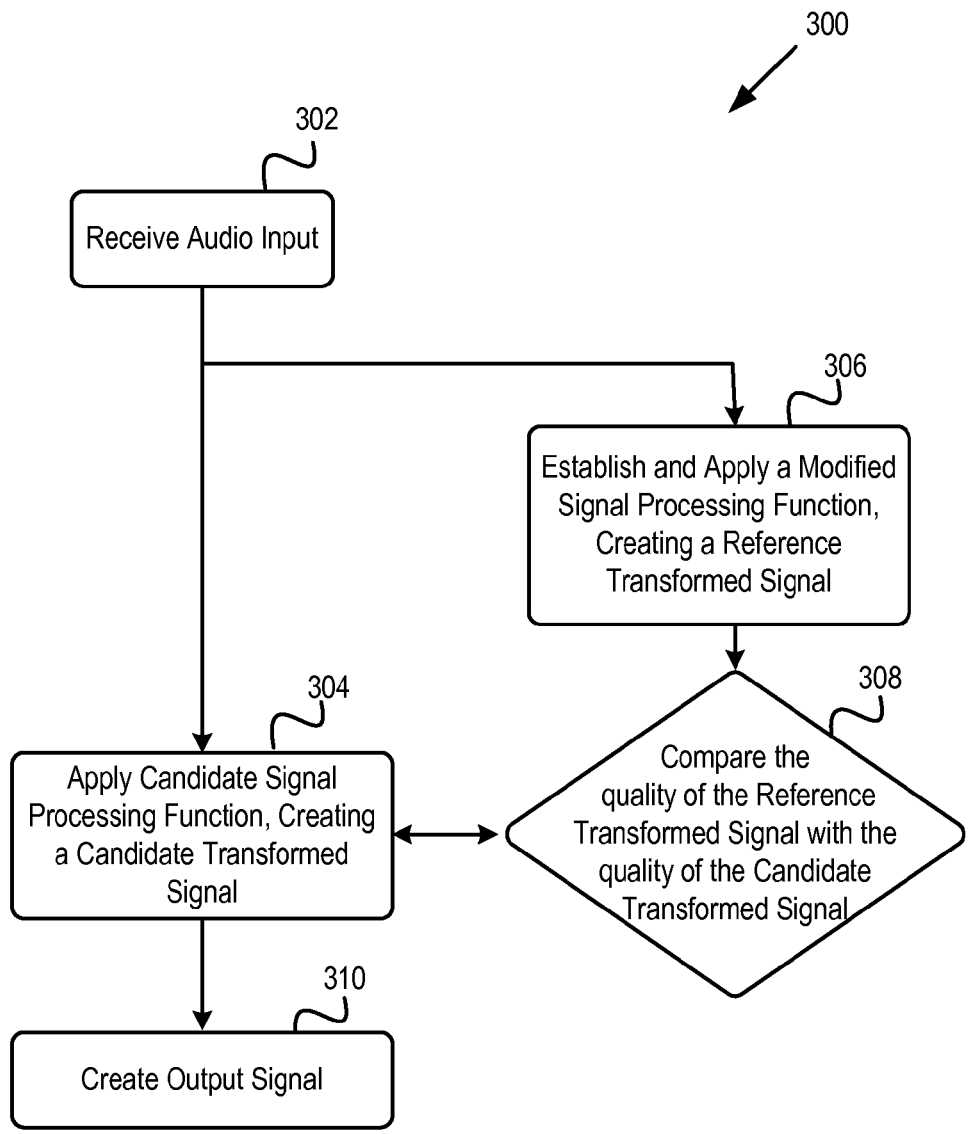
FIG. 3 is a flow diagram of one embodiment of an automatic sound optimizer method.

The transforming the input signal into the output performed by the sound processor 230 includes methods similar to method 300 described with respect to FIG. 3.

In some situations, at least one sound processor located in a remote computing device processes a portion of the signal. In such cases, data is transmitted via an input/output device 260. The input/output device 260 is, for example, a remote computer terminal suitable for issuing instructions to the one or more processors. The input/output device 260 transmits the request to the data interface 236 via a communication connection 265. The communication connection 265 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, and the like.

The data interface 236 transmits data to the one or more processors 230. The data transmitted includes both received audio signals and an indication of a signal processing mode. Upon receiving the data, the one or more processors performs the methods disclosed herein. The one or more processors continue to process the data in this manner until the recipient transmits a request via the input/output device 260 to return to normal (or default) signal processing.

Various modifications can be made to the hearing prosthesis 220 illustrated in FIG. 2. For example, in some embodiments, the hearing prosthesis 220 includes additional or fewer components arranged in any suitable manner. In some examples, the hearing prosthesis 220 includes other components to process external audio signals, such as components that measure vibration in the skull caused by audio signals and/or components that measure electrical output of portions of a person's hearing system in response to audio signals. Further, depending on the type and design of the hearing prosthesis 220, the illustrated components may be enclosed within a single operational unit or distributed across multiple operational units (e.g., two or more internal units or an external unit and an internal unit).

3. Sample Methods

FIG. 3 is a flow diagram of one embodiment of the automatic sound optimizer method 300 presented herein. Some examples of method 300 are performed by example hearing prosthesis 101 in FIG. 1A or by the example cochlear implant 150 shown in FIG. 1B. Additionally, other types of hearing prostheses can implement method 300 as well. Although the blocks are illustrated in a specific order, in some embodiments, these blocks are also performed in a parallel order, sequential order, and/or in another order that differs from that described herein. Also, the various blocks may be combined into fewer blocks, divided into additional blocks, and/or eliminated based upon the desired implementation.

Additionally, method 300 may be performed with various different timings. For example, in one embodiment, during the operation of the hearing prosthesis, the prosthesis performs method 300 continuously. In another embodiment, the hearing prosthesis performs method 300 at specific time intervals. In a further embodiment, the hearing prosthesis performs method 300 when the ambient audio conditions change. For example, when the hearing prosthesis detects a change in the ambient audio conditions, such as the change in ambient audio conditions when a prosthesis recipient walks into a noisy room, and responsively iterate the parameters to help to optimize sound quality.

In yet another embodiment, the hearing prosthesis performs method 300 based on an instruction received from either an interaction from a recipient or from an external input. For example, method 300 is performed in response to an interaction with a graphical user interface, button interface or by other interface on an external device. Further, a portion of method 300 is carried out on a processor located within a computing device external to the body-worn hearing prosthesis, such as a computer. The processor in the computing device calculates parameters for a sound processing mode and the associated quality. For example, in one embodiment, a prosthesis recipient selects a music file on his or her computing device to be played at a later time through his or her hearing prosthesis. The hearing prosthesis responsively switches to a music mode and the processor performs method 300. Further, in some embodiments, the processor performs method 300 in full on the computing device. The computing device allows the recipient to both (i) listen to the music file through simulated processing after optimization and (ii) upload such parameters associated with the music mode on the hearing prosthesis.

Method 300 begins at block 302, when the prosthesis receives an audio input. In one embodiment, an audio input is received when the prosthesis detects an acoustic signal with an acoustic detector (i.e. a transducer or microphone). In some embodiments, the acoustic detector is located within the hearing prosthesis. For example, the acoustic detector is located inside the housing of the external portion of a cochlear implant device (e.g., 102 of FIG. 1B). In many embodiments, the audio input is an acoustic wave. However, the disclosed embodiments are not limited to only acoustic waves. For example, in some embodiments, an audio input is provided with a radio signal.

In additional embodiments, the audio input is received from a separate device. For example, the hearing prosthesis receives an audio signal from a Bluetooth device. Additionally, the audio input can be from a radio signal, optical signal, or acoustic wave. In yet another example, the audio input comes from a wired connection to another device. For example, the prosthesis recipient connects a portable audio player to an input of the prosthesis.

At block 302, the acoustic detector (or other receiver) receives and audio input. In embodiments where the audio input is not an acoustic wave, a receiver device is used to create the electrical signal representing the audio input for use with method 300. For example, if the audio input is provided by radio waves, an antenna and radio receiver converts the received radio signal into an electrical signal representing the audio input. At block 302, the processor outputs an electrical signal representative of the audio input, regardless of the source of the input.

In some additional embodiments, two separate audio sources provide the audio input at block 302. For example, a hearing prosthesis has two microphones. In this example, each microphone provides its own signal as the audio input at 302. In a different example, a radio link provides two audio streams as inputs at 302. The two audio streams from the radio link will be processed as audio inputs.

At block 304, a processor in the hearing prosthesis applies a candidate signal processing function to the electrical signal representative of the audio input that was created at block 302, creating a candidate transformed signal. The candidate transformed signal is created based on the candidate signal processing function and the electrical signal provided by block 302. The candidate signal processing function is a signal processing function that includes a set of signal processing parameters. The signal processing function is selected either (i) by a recipient of the hearing prosthesis or (ii) automatically by a processor within the hearing prosthesis.

In one embodiment, the recipient selects a specific signal processing function based on the environment around the recipient or based on the type of sound to which the recipient is listening. For example, if the recipient goes outside, he or she may enable a wind-noise reduction mode of the hearing prosthesis. In another embodiment, the recipient may enable a beam-forming mode in a noisy environment. The beam-forming mode may be able to isolate a specific audio source to which the recipient wishes to listen. Additionally, in some embodiments, the hearing prosthesis selects a sound processing mode automatically. In one example, the hearing prosthesis both recognizes that an audio input contains wind noise, based on audio attributes of the audio input. Further, the hearing prosthesis responsively enables the wind-noise reduction mode.

In one aspect, each signal processing mode has at least one associated signal processing parameter. In turn, the signal processing parameter defines how the signal processing mode instructs the processor to modify an input signal when the specific signal processing mode is enabled. For example, in a wind noise reduction mode, the signal processing parameter will define how the hearing prosthesis removes wind noise. In some embodiments, the signal processing parameter can be varied to account for different noises produced by the wind. Either a processor, or the prosthesis recipient, controls the parameter variations. Further, in some embodiments, a processor helps optimize the parameters associated with a signal processing mode to provide increased sound quality.

Other signal processing modes may be used with the method disclosed herein as well, such as beam-forming mode, voice enhancement mode, feedback reduction mode, compression timing mode and music mode. Additionally, some sound processing modes used with method 300 include multiple inputs and outputs. For example, a beam-forming signal processing mode uses multiple inputs to create a single output. In the beam-forming signal processing mode, the processor applies weighting criteria to the multiple input signals to form a virtual beam. Through beam forming, undesirable signals are removed from the combination of the two input signals. Beam forming also allows the prosthesis to isolate a desired input signal. For example, in a noisy room, a beam-forming algorithm attempts to isolate the voice of person speaking to the prosthesis recipient from the a group of voices present in the room.

In another embodiment with two microphones, a first microphone receives a signal with a component to be amplified and the second microphone receives a signal that is mainly background noise. Further, the first microphone has a beam pattern designed to capture sound in the direction the prosthesis recipient is looking Additionally, the second microphone has a beam pattern that is omnidirectional and designed to capture all ambient sound. The signal processing is configured to remove the signal produced by the second microphone from the signal produced by the first microphone. Thus, ambient noise, as captured by the second microphone, is removed from the signal produced by the directional microphone.

In additional embodiments, a sound processor within the hearing prosthesis is able to identify a desirable sound processing mode based on audio attributes of the received audio input. For instance, the processor measures audio parameters, such as amplitude and frequency components, of the audio input to determine a suitable sound processing mode. For example, the processor recognizes a poor signal-to-noise ratio and responsively enable a noise reduction mode. In an additional example, the processor identifies wind noise based on the audio parameters of the audio input. The processor responsively enables wind-noise reduction mode.

Once at least one sound processing mode is selected, either automatically by the prosthesis or by a recipient, block 304 and block 306 are performed. At block 304, the processor creates a candidate signal processing function based on the selected sound processing mode. Further, the processor transforms the electrical signal representing the audio input into a candidate transformed signal with the candidate signal processing function. For instance, the transformation involves modifying at least one audio attribute of the electrical signal representing the audio input. In turn, the audio attributes are modified based on signal processing parameters associated with the candidate signal processing function. For example, the audio attributes modified includes acoustic gain tables, frequency response curves, and other audio parameters.

By way of example, transforming the electrical signal representing the audio input into a candidate transformed signal, as performed at block 304, includes applying a candidate signal processing function to the input signal, so as to create a candidate transformed signal. The candidate signal processing function that is part of the transformation includes one or more candidate signal processing attributes that alter one or more parameters of the input signal so as to create a candidate transformed signal.

Block 304 is followed by block 310, where the candidate transformed signal is transformed into an output. The output can take many different forms, possibly dependent on the specific type of hearing prosthesis implementing method 300. In one aspect, where the hearing prosthesis is an acoustic hearing aid, the audio output will be an acoustic signal. Thus, the output is an electronic signal provided to a speaker to create the audio output. In another embodiment, where the hearing prosthesis is a cochlear implant, the output of the hearing prosthesis is a current supplied by an electrode (such as electrode assembly 160 of FIG. 1B). Thus, the output from 310 is an electrical signal provided to the output electronics that control the electrode assembly. In yet another embodiment, the output is simply the candidate transformed signal from block 304. In some embodiments, the output is supplied to further electrical components.

Additionally, at block 306 the processor establishes a modified signal processing function operating in the same signal processing mode as block 304. To establish the modified signal processing function, the sound processor adjusts one or more of the candidate signal processing parameters of the candidate signal processing function. For example, in a wind-noise reduction mode, to create the modified signal processing the processor adjusts the frequency response parameter. Once the parameter is adjusted, the processor has created a modified signal processing function.

At block 306, the processor varies the processing parameters associated with the modified signal processing function is several different ways. In a first mode, the processor varies parameters based on a random number. For example, with each iteration of method 300, the processor either increases or decreases at least one of the parameters based on a random number. In a second mode, the processor calculates the effect adjusting the parameter has on the output. For example, the processor calculates if the adjustment of the parameter associated with each variation made the quality of the reference transformed signal increase or decrease. Additionally, in some embodiments, the processor adapts the variation of the parameters to continually increase the sound quality of the output with each iterative variation.

Similar to block 304, at block 306 the processor will apply the signal processing function the audio input signal. The processor will receive the electrical signal representing the audio input from block 302 and transform it into a reference transformed signal. For instance, the transformation occurs when the processor changes at least one audio attribute of the electrical signal representing the audio input based on the modified signal processing function. The only difference between block 304 and block 306 is that the parameters applied to the electrical signal are different at the respective blocks. At block 306, the processor modifies audio attributes based on the modified set of signal processing parameters associated with the modified signal processing function. Additionally, at block 306 the sound processor applies the modified signal processing function to the input signal so as to create a reference transformed signal.

Thus, at both blocks 304 and 306 the processor creates a signal based on the electrical signal representing the audio input. However, each block uses a different set of signal processing parameters. Thus, the reference transformed signal created by the processor at block 306 is not exactly the same as the candidate transformed signal created by the processor at block 304.

At block 308, the processor receives both the reference transformed signal created at block 306 and the candidate transformed signal created at block 304. Further, the processor makes a determination as to whether a quality of the reference transformed signal is better than a quality of the candidate transformed signal. In one embodiment, the processor makes a determination of quality determination based on multiple criteria. For example, in some embodiments, the determination of quality is based in part on a set of recipient-specific parameters. For example, in some embodiments, the hearing prosthesis is programmed with specific parameters for a prosthesis recipient. The recipient-specific parameters typically include acoustic gain tables, frequency response curves, and other audio parameters specific to a given recipient. In some embodiments, the recipient-specific parameters are based on a hearing impairment associated with a recipient.

In practice, the recipient-specific parameters typically are based on a hearing impairment associated with a recipient, such as conductive hearing loss. For example, when the processor in the hearing prosthesis determines the quality of the reference transformed signal and the candidate transformed signal, the prosthesis uses information associated with the recipient-specific parameters to determine the quality. If a recipient has conductive hearing loss, the recipient-specific parameters indicate a frequency band in which the recipient requires additional sound amplification. In this specific example, the prosthesis will help to optimize the sound quality based on the recipient-specific required amplification. Further, in some embodiments, the hearing prosthesis includes a calibration mode that enables the recipient to select a setting that controls the recipient-specific parameters.

In an embodiment, if the determination is that quality of the reference transformed signal is better than the quality of the candidate transformed signal, the processor will substitute the modified signal processing function parameters for the candidate signal processing function parameters. However, if the determination indicates that the quality of the reference transformed signal is not better than the quality of the candidate transformed signal, then the processor continues to provide the candidate transformed signal to create the output signal at block 310.

In some additional embodiments, at block 306 the processor iteratively revises the processing parameters associated with the modified signal processing function. With each iteration, the processor calculates of the quality of the reference transformed signal created with the revised the processing parameters. Responsive to a calculation indicating an increase in the quality of the reference transformed signal, the processor then compares the quality of the candidate transformed signal with the quality of the reference transformed signal at block 308.

In the numerous embodiments, the processor uses various different methods to calculate the quality of each signal. In some examples, the quality calculation is objective (i.e. calculated by a processor) or subjective (i.e. the recipient selects which signal sounds better). An example subjective quality calculation is a hearing prosthesis with a calibration mode in which the recipient selects which of the two signal processing functions sounds better. Thus, the prosthesis uses a subjective measure of quality. Conversely, in some embodiments, the processor uses method 300 to objectively calculate which of the two signals is of a higher quality. The processor calculates an objective sound quality value using any of the various methods of sound quality measurement.

The signal with higher quality value is generally the more desirable signal. Thus, if the processor uses the candidate signal processing function to create the more desirable (e.g., the higher quality) signal, then the processor will continue to output the candidate transformed signal. However, if the processor uses the modified signal processing function to creates the more desirable signal, then the processor will update the candidate signal processing function with the parameters of the modified signal processing function parameters. Therefore, the candidate transformed signal would be equal to the reference transformed signal. By revising the parameters, the processor would continue to provide the higher quality output.

For the disclosed embodiments, no specific algorithm for sound quality is required for method 300. In fact, the sound quality calculation algorithm varies depending on the sound processing mode. For example, in a wind-noise reduction mode, the sound-quality algorithm helps to optimize for the lowest overall noise level. However, in the beam forming mode, the sound-quality algorithm helps to optimize based on the best quality of speech delivered. In yet another embodiment, the sound-quality algorithm helps to optimize based on the best quality of music delivered. Further, any algorithm that can be used to calculate sound quality of a signal may be used with block 308.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A hearing prosthesis system comprising:
a first receiver arranged to receive an input signal, the input signal having at least one audio attribute;
output circuitry for providing an output to a user; and
a processor arranged to transform the input signal into a transformed signal and to provide the transformed signal to the output circuitry, wherein the output circuitry provides the output based on the transformed signal,
wherein transforming the input signal into the transformed signal comprises (i) applying a candidate signal processing function to the input signal to generate a candidate transformed signal having a first modification of the audio attribute, (ii) applying a reference signal processing function to the input signal to generate a reference transformed signal having a second modification of the audio attribute, the second modification being different than the first modification such that the candidate transformed signal is different than the reference transformed signal, (iii) determining which of the candidate transformed signal and reference transformed signal is better quality, and (iv) selecting as the transformed signal the determined better quality signal and not the determined lower quality signal,
wherein providing the transformed signal to the output circuitry comprises providing the determined better quality signal and not the determined lower quality signal to the output circuitry, and wherein the output circuitry provides the output based on the determined better quality signal and not the determined lower quality signal,
wherein the processor repeatedly conducts the transforming, wherein, in a first instance of conducting the transforming, the transformed signal is the candidate transformed signal, wherein, in a second instance of conducting the transforming, the transformed signal is the reference transformed signal, and wherein in the second instance of conducting the transforming, the candidate signal processing function has one or more candidate signal processing parameters and the reference signal processing function has one or more reference signal processing parameters different than the one or more candidate signal processing parameters, and wherein in the second instance of conducting the transforming, the processor determines that the reference transformed signal is better quality than the candidate transformed signal, and the processor responsively substitutes the one or more reference signal processing parameters for the one or more candidate signal processing parameters, so as to have a modified candidate signal processing function for a next instance of conducting the transforming.

2. The hearing prosthesis system of claim 1, wherein the processor is further arranged to operate in a processing mode selected from a group of available processing modes, wherein each processing mode initially defines one or more of the candidate signal processing parameters or the reference signal processing parameters.

3. The hearing prosthesis system of claim 1, further comprising a second receiver, wherein the second receiver is arranged to receive audio.

4. The hearing prosthesis system of claim 3, wherein the processor is further configured to receive a supplemental signal representing the audio received by the second receiver, the supplemental signal having one or more audio attributes.

5. The hearing prosthesis system of claim 4, wherein the processor is arranged to transform the supplemental signal into a supplemental transformed signal and to provide the supplemental transformed signal to the output circuitry, wherein the output circuitry provides the output based also on the supplemental transformed signal,
wherein transforming the supplemental input signal into the supplemental transformed signal further comprises (i) applying the candidate signal processing function to the supplemental signal to generate a supplemental candidate transformed signal having a first modification of the audio attribute, (ii) applying the reference signal processing function to the supplemental signal to generate a supplemental reference transformed signal having a second modification of the audio attribute, the second modification being different than the first modification, (iii) determining which of the supplemental candidate transformed signal and supplemental reference transformed signal is better quality, and (iv) selecting as the supplemental transformed signal the determined better quality supplemental signal and not the determined lower quality supplemental signal, wherein providing the supplemental transformed signal to the output circuitry comprises providing the determined better quality supplemental signal and not the determined lower quality supplemental signal to the output circuitry, and wherein the output circuitry provides the output based on the determined better quality supplemental signal and not the determined lower quality supplemental signal.

6. The hearing prosthesis system of claim 4, wherein transforming the input signal into the transformed signal further comprises applying the candidate signal processing function to both the input signal and the supplemental signal so as to produce the candidate transformed signal, and applying the reference signal processing function to both the input signal and the supplemental signal so as to produce the reference transformed signal.

7. The hearing prosthesis system of claim 1, wherein the processor is located in a computer external to a hearing prosthesis device.

8. The hearing prosthesis system of claim 1, wherein the processor is located within a hearing prosthesis device.

9. The hearing prosthesis system of claim 1, wherein determining which of the candidate transformed signal and reference transformed signal is better quality is based, at least in part, on recipient-specific parameters, wherein the recipient-specific parameters are based on a hearing impairment associated with a user.

10. The hearing prosthesis system of claim 1, wherein determining which of the candidate transformed signal and reference transformed signal is better quality is based, at least in part, on recipient-specific parameters, wherein the recipient-specific parameters are based on a setting selected by a user.

11. A method comprising:
receiving an input signal representing an audio signal received by a receiver, the input signal having an audio attribute;
transforming the input signal into a transformed signal;
providing the transformed signal as an output that can be perceived as sound; and
performing at least a first instance and a second instance of each of the receiving, transforming, and providing,
wherein transforming the input signal into the transformed signal comprises:
  applying a candidate signal processing function to the input signal to generate a candidate transformed signal having a first modification of the audio attribute;
  applying a reference signal processing function to the input signal to generate a reference transformed signal having a second modification of the audio attribute, the second modification being different than the first modification such that the candidate transformed signal is different than the reference transformed signal;
  determining which of the candidate transformed signal and reference transformed signal is better quality; and
  selecting as the transformed signal the determined better quality signal and not the determined lower quality signal,
wherein, in the first instance of the transforming, the transformed signal is the candidate transformed signal,
wherein, in the second instance of the transforming, the transformed signal is the reference transformed signal,
and wherein providing the transformed signal as the output includes providing the determined better quality signal as the output and not providing the determined lower quality signal as the output.

12. The method of claim 11, further comprising selecting a processing mode from a group of available processing modes, wherein each processing mode initially defines one or more signal processing parameters that are used by at least one of the candidate signal processing function to generate the candidate transformed signal or by the reference signal processing function to generate the reference transformed signal.

13. The method of claim 11, further comprising receiving a supplemental signal representing audio received by a second receiver, the supplemental signal having an audio attribute.

14. The method of claim 13, further comprising:
applying the candidate signal processing function to the supplemental signal to generate a supplemental candidate transformed signal having a first modification of the audio attribute;
applying the reference signal processing function to the supplemental signal to generate a supplemental reference transformed signal having a second modification of the audio attribute, the second modification being different than the first modification;
determining which of the supplemental candidate transformed signal and supplemental reference transformed signal is better quality; and
outputting as a supplemental transformed signal the determined better quality supplemental signal and not the determined lower quality supplemental signal.

15. The method of claim 13, wherein transforming the input signal into the transformed signal further comprises applying the candidate signal processing function to both the input signal and the supplemental signal so as to produce the candidate transformed signal, and applying the reference signal processing function to both the input signal and the supplemental signal so as to produce the reference transformed signal.

16. The method of claim 11, wherein the transforming is performed by a processor, and wherein the processor is located in a computer external to a hearing prosthesis device.

17. The method of claim 11, wherein the transforming is performed by a processor, and wherein the processor is located within a hearing prosthesis device.

18. The method of claim 11, wherein determining which of the candidate transformed signal and reference transformed signal is better quality is based, at least in part, on recipient-specific parameters, wherein the recipient-specific parameters are based on a hearing impairment associated with a recipient.

19. The method of claim 11, wherein determining which of the candidate transformed signal and reference transformed signal is better quality is based, at least in part, on recipient-specific parameters, wherein the recipient-specific parameters are based on a setting selected by a recipient.

20. A medical implant comprising:
a microphone arranged to:
  receive an audio signal; and
  convert the audio signal into an electrical input signal having one or more audio attributes;

output circuitry for providing an output to a recipient of the implant; and a processor arranged to receive the electrical input signal, to transform the electrical input signal into a transformed signal, and to convey the transformed signal to the output circuitry for providing the output based on the transformed signal, wherein transforming the electrical input signal into the transformed signal comprises:
(a) establishing a candidate signal processing function based on a selected sound processing mode, wherein the candidate signal processing function has one or more candidate signal processing parameters;
(b) establishing a modified signal processing function based on the selected sound processing mode, wherein the modified signal processing function has one or more modified signal processing parameters, and wherein the modified signal processing parameters are different than the candidate signal processing parameters;
(c) applying the candidate signal processing function to the electrical input signal so as to produce a candidate transformed signal, wherein the candidate signal processing function modifies at least one audio attribute of the electrical input signal, and
(d) applying the modified signal processing function to the electrical input signal so as to produce a reference transformed signal, wherein the modified signal processing function modifies at least one audio attribute of the electrical input signal, wherein the candidate transformed signal is different than the reference transformed signal,
(e) making a determination of a quality of the candidate transformed signal, wherein the determination of quality is based on a set of recipient-specific parameters,
(f) making a determination of a quality of the reference transformed signal, wherein the determination of quality is based on the set of recipient-specific parameters,
(g) in a first instance, determining that the quality of the reference transformed signal is better than the quality of the candidate transformed signal, and responsively providing the reference transformed signal as the transformed signal and substituting the modified signal processing function parameters for the candidate signal processing function parameters, and
(h) in a second instance, determining that the quality of the reference transformed signal is not better than the quality of the candidate transformed signal, and responsively providing the candidate transformed signal as the transformed signal.

21. The medical implant of claim 20, wherein the processor is further arranged to operate in a processing mode selected from a group of available processing modes, wherein each processing mode initially defines one or more of the candidate signal processing parameters or the modified signal processing parameters.

22. The medical implant of claim 20, further comprising a second microphone, wherein the second microphone is arranged to receive a second audio signal and to convert the second audio signal into a supplemental signal having one or more audio attributes.

23. The medical implant of claim 22, wherein the processor is further configured to receive the supplemental signal, to transform the supplemental signal into a supplemental transformed signal, and to convey the supplemental transformed signal to the output circuitry for providing the output based on the supplemental transformed signal.

24. The medical implant of claim 23, wherein transforming the supplemental signal into the supplemental transformed signal further comprises:
(i) applying the candidate signal processing function to the supplemental signal so as to produce a supplemental candidate transformed signal, wherein the candidate signal processing function modifies at least one audio attribute of the supplemental signal, and
(j) applying the modified signal processing function to the supplemental signal so as to produce a supplemental reference transformed signal, wherein the modified signal processing function modifies at least one audio attribute of the supplemental signal,
(k) making a determination of a quality of the supplemental candidate transformed signal, wherein the determination of quality is based on a set of recipient-specific parameters,
(l) making a determination of a quality of the supplemental reference transformed signal, wherein the determination of quality is based on a set of recipient-specific parameters,
(m) if the quality of the supplemental reference transformed signal is better than the quality of the supplemental candidate transformed signal, then substituting the modified signal processing function parameters for the candidate signal processing function parameters and repeating from (i), and
(n) if the quality of the supplemental reference transformed signal is not better than the quality of the supplemental candidate transformed signal, then providing the supplemental candidate transformed signal as the supplemental transformed signal.

25. The medical implant of claim 23, wherein transforming the input signal into the transformed signal further comprises applying the candidate signal processing function to both the electrical input signal and the supplemental signal so as to produce the candidate transformed signal, and applying the reference signal processing function to both the input signal and the supplemental signal so as to produce the reference transformed signal.

26. The medical implant of claim 20, wherein the processor is located in a computer external to a hearing prosthesis device.

27. The medical implant of claim 20, wherein the recipient-specific parameters are based on a hearing impairment associated with the recipient.

* * * * *